United States Patent [19]

Laine

[11] Patent Number: 4,566,084

[45] Date of Patent: Jan. 21, 1986

[54] ACOUSTIC VELOCITY MEASUREMENTS IN MATERIALS USING A REGENERATIVE METHOD

[75] Inventor: Edwin F. Laine, Alamo, Calif.

[73] Assignee: The United States of America as represented by the United States Department of Energy, Washington, D.C.

[21] Appl. No.: 429,920

[22] Filed: Sep. 30, 1982

[51] Int. Cl.⁴ .............................................. G01V 1/28
[52] U.S. Cl. ...................................... 367/49; 73/597; 367/75
[58] Field of Search .................. 367/32, 41, 49, 75, 367/13, 25, 31, 37, 43, 57, 65, 75, 86; 73/594, 597; 181/101, 102, 104, 108

[56] References Cited

U.S. PATENT DOCUMENTS

| | | |
|---|---|---|
| 2,231,243 | 2/1941 | Beers . |
| 2,723,387 | 11/1955 | Slavin, III . |
| 2,754,492 | 7/1956 | Parker .................................. 367/189 |
| 3,311,875 | 3/1967 | Geyer et al. . |
| 3,330,375 | 7/1967 | White . |
| 3,938,072 | 2/1976 | Baird et al. . |
| 4,105,993 | 8/1978 | Grassy et al. . |
| 4,128,011 | 12/1978 | Savage . |

FOREIGN PATENT DOCUMENTS 901894  1/1982  U.S.S.R. .

Primary Examiner—Salvatore Cangialosi
Assistant Examiner—K. R. Kaiser
Attorney, Agent, or Firm—Clifton E. Clouse, Jr.; Roger S. Gaither; Judson R. Hightower

[57] ABSTRACT

Acoustic energy is propagated through earth material between an electro-acoustic generator and a receiver which converts the received acoustic energy into electrical signals. A closed loop is formed by a variable gain amplifier system connected between the receiver and the generator. The gain of the amplifier system is increased until sustained oscillations are produced in the closed loop. The frequency of the oscillations is measured as an indication of the acoustic propagation velocity through the earth material. The amplifier gain is measured as an indication of the acoustic attenuation through the earth materials. The method is also applicable to the non-destructive testing of structural materials, such as steel, aluminum and concrete.

19 Claims, 1 Drawing Figure

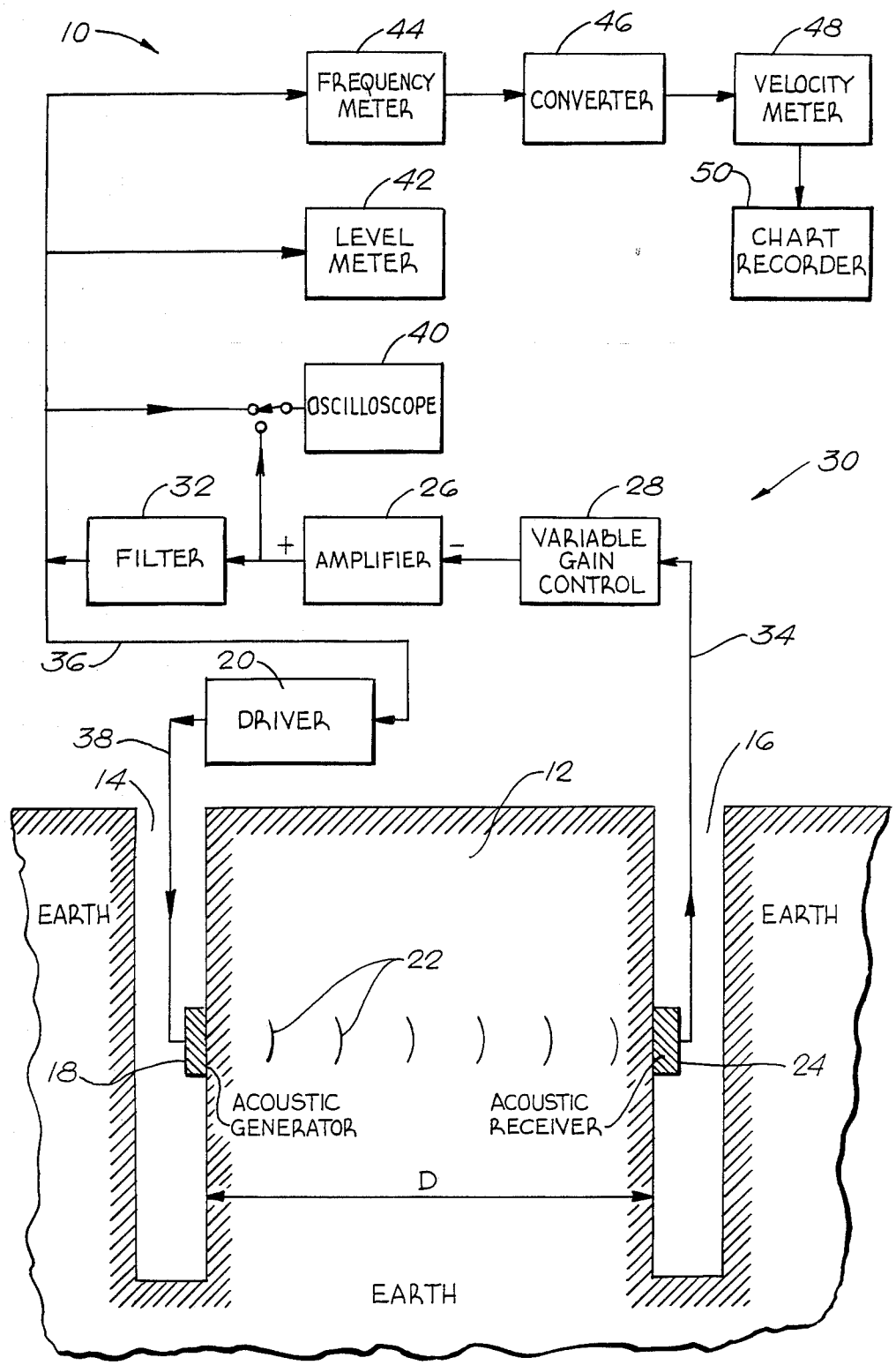

ACOUSTIC VELOCITY MEASUREMENTS IN MATERIALS USING A REGENERATIVE METHOD

The U.S. Government has rights in this invention pursuant to Contract No. W-7405-ENG-48 between the United States Department of Energy and the University of California.

DESCRIPTION

Field of the Invention

This invention relates generally to characterizing materials by measuring the propagation of acoustic energy through such materials. More specifically, the invention relates to geological exploration in which acoustic energy is propagated through a portion of the earth to characterize the materials in the earth through which the acoustic energy is propagated.

BACKGROUND OF THE INVENTION

It is a common practice to characterize materials by sending an energy wave, comprising some form of energy, such as acoustic energy, through the material to be characterized. This technique is used in geology, for characterizing a volume of earth in search of such materials as oil and water deposits. The techique is also used in the technology relating to non-destructive evaluation of structural materials, to detect imperfections, such as voids, cracks, or inclusions, in materials such as steel, aluminum and concrete.

This technique employs an energy source for generating an energy pulse signal which travels through the material to be characterized. A receiver is employed for receiving and interpreting the pulse or signal. The distance between the source and the receiver is known, as is the energy of the transmitted pulse. By measuring the time it takes for the signal to travel from the source to the receiver, the velocity of propagation can be computed and compared with tables of known characteristics of materials. In this way, it is possible to characterize the type of material. By making a series of measurements along different paths through the material, and by detecting and characterizing echos, it is possible to detect and characterize irregularities in the material.

In geological exploration, the energy source of the receiver may be placed at different locations on the surface of the earth, or in first and second bore holes which are spaced apart by a known distance. The source or generator may produce signals in the form of a series of discrete pulses which travel the known distance from the generator to the receiver. Typically, the generator may consist of such devices as dynamite or other explosive charges, or a source of electric sparks. Such generators may produce pulses comprising compression or pressure waves, rarification waves, and shear waves having both horizontal and vertical components, as desired. Shear waves are often used as the energy pulses because sheer waves travel at approximately one half to one third the rate of speed of compression waves, thus allowing more time for the receiver to receive and analyze the pulses.

The existing techniques suffer from problems and disadvantages, including operational difficulties in setting up and using the existing techniques, difficulties in making accurate measurements of the propagation times of the pulses, and difficulties in interpretation of the test data, so that interpretation by highly skilled personnel is required. The comparison of the test data with the known material characteristics is also difficult.

SUMMARY OF THE INVENTION

One object of the present invention is to provide a new and improved method of characterizing materials by causing acoustic energy to be progagated through such materials.

A further object is to provide such a new and improved method which is more accurate, simpler and easier to employ than heretofore.

Another object is to provide a new and improved apparatus for characterizing materials by causing acoustic energy to be propagated through such materials.

To accomplish these and other objects, the present invention preferably provides a method of characterizing materials, comprising the steps of supplying acoustic energy at a first location to the material to be characterized, the acoustic energy being propagated through the material, receiving the acoustic energy at a second location on the material and converting the received acoustic energy into electric signals, amplifying the electrical signals to produce amplified electrical energy, converting the amplified electrical energy into such acoustic energy, the amplifying step being carried out with sufficient regenerative amplification to produce oscillations of the electrical energy and the acoustic energy, and indicating the frequency of the oscillations as an indication of the character of the material.

The indicating step preferably includes measuring the frequency of the oscillations, and converting the frequency into a indication of the velocity of the propagation of the acoustic energy through the material. Such conversion may be accomplished by multiplying the frequency by the distance of acoustic propagation through the material.

The amplifying step preferably includes adjusting the regenerative amplification to produce sustained oscillations.

The gain factor of such regenerative amplification is preferably employed as a further indication of the character of the material.

The acoustic energy is preferably produced in the form of a generally sinusoidal acoustic shear wave for propagation through the material.

The present invention preferably provides apparatus for characterizing materials, such apparatus comprising an acoustic generator for converting electrical energy into acoustic energy and for supplying such acoustic energy to the material to be characterized at a first location, the acoustic energy being propagated through the material, an acoustic receiver for receiving the acoustic energy from the material at a second location and for converting the received acoustic energy into electrical signals, an amplifier system connected between the receiver and the transmitter for amplifying the electrical signals from the receiver and supplying corresponding amplified electrical energy to the transmitter, the amplifier system having sufficient regenerative gain to produce oscillations which indicate the characteristics of the material through which the acoustic energy is being transmitted, and indicating means for indicating the character of such oscillations as an indication of the character of such material.

Such indicating means preferably include velocity indicating means for measuring the frequency of the oscillations and for converting the frequency into an indication of velocity by multiplying the frequency by the distance through the material between the transmitter and the receiver.

Such amplifier system preferably includes a calibrated gain control for adjusting the gain of the amplifier system to produce sustained oscillations while indicating the magnitude of such gain as a further indication of the character of the material.

Such generator preferably comprises means for generating generally sinusoidal acoustic shear waves for propagation through the material. Such receiver preferably comprises a geophone.

BRIEF DESCRIPTION OF THE DRAWING

Further objects, advantages and features of the present invention will appear from the following description, taken with the accompanying drawing, in which the single FIGURE is a diagrammatic elevational view, partly in section, showing a preferred embodiment of apparatus constructed in accordance with the present invention.

DETAILED DESCRIPTION OF THE ILLUSTRATIVE EMBODIMENT

As just indicated, the drawing illustrates apparatus 10 for indicating and measuring the characteristics of material 12, which in this case takes the form of a volume of earth material. Thus, the apparatus 10 is intended particularly for geological exploration. However, the apparatus of the invention can also be used for nondestructive testing of various structural materials.

As shown in section in the drawing, the earth material 12 is preferably formed with first and second bore holes 14 and 16 which are spaced apart by a selected distance D. The bore holes 14 and 16 may be drilled or otherwise formed in the earth material 12. An acoustic generator 18 is mounted in the first bore hole 14 and is suitable clamped against the side of the bore hole 14, to supply acoustic energy to the earth material 12. The generator 18 is preferably of any known or suitable construction, adapted to convert electrical energy into acoustic energy, preferably in the form of generally sinusoidal shear waves. Thus, for example, the generator 18 may take the form of a Mark Products vertical shear wave generator. A driver or power amplifier 20 supplies electrical power to the generator 18, so that it produces acoustical waves or pulses 22, which are propagated through the earth material 12.

The acoustic energy or waves 32 travel through the earth material 12 and are detected by a receiver 24 which is preferably mounted in the second bore hole 16 and is clamped against the side of the bore hole, in engagement with the earth material 12, to receive the acoustic energy at a reduced or attenuated level.

The receiver 24 constitutes a transducer for converting the received acoustic energy into electrical signals which are supplied to the input of an amplifier 26 having a variable gain control 28. The receiver 24 may be in the form of a vertical geophone.

The output of the amplifier 26 is supplied to the input of the driver 20 to form a closed loop 30 which also preferably includes a filter 32. It will be understood that the sequence of the amplifier 26, the gain control 28, and the filter 32 in the closed loop may be varied. The phasing or polarity of the amplifier 26 in the closed loop is preferably such that the closed loop provides regenerative positive feedback or amplification.

The closed loop 30 may comprise a transmission line 34 for carrying the electrical signals from the receiver 24 to the amplifier 26, a second transmission line 36 for carrying the amplified electrical signals between the amplifier 26 and the driver 20, and a third transmission line 38 for carrying the electrical power between the driver 20 and the transmitter 18.

The illustrated apparatus 10 comprising indicating means, which may include an oscilloscope 40, a level meter 42, and a frequency meter 44. As shown, the oscilloscope 42 is provided with a selector switch 46, whereby the input of the oscilloscope 40 may be connected to either the output of the amplifier 26 or the output of the filter 32. In this case, a level meter 42 is connected to the output of the filter 32. The frequency meter 44 is also connected to the output of the filter 32. The oscilloscope 40 may be employed to measure the voltage of the amplified electrical signals from the amplifier 26 or the filter 32. The oscilloscope 40 may also be employed to indicate or measure the frequency of the amplified electrical signals, while also indicating the waveform of such signals.

The level meter 42 indicates or measures the voltage of the amplified electrical signals. The frequency of the amplified electrical signals is indicated or measured by the frequency meter 44.

In accordance with the method of the present invention, the amplifier 26 in the closed loop 30 provides regenerative amplification. The variable gain control 28 is preferably adjusted so that such regenerative amplification produces sustained oscillations in the closed loop 30. The frequency of such oscillations is then indicated or measured by the oscilloscope 40 or the frequency meter 44, as an indication of the characteristics of the earth material 32 through which the acoustical waves 22 are propagated between the transmitter 18 and the receiver 24. The frequency of the oscillations is proportional to the velocity with which the acoustic energy is propagated through the earth material 12. The actual velocity can be determined or computed by multiplying the frequency by the distance D between the transmitter 18 and the receiver 24, through the earth material 12. The velocity is derived from the following relationships:

$$v = d/t$$

where $v$=velocity, $d$=distance, $t$=time and $t = 1/f$ where $f$=frequency. Then: $v = df$.

As shown, a converter 46 is connected between the frequency meter 44 and a velocity meter 48. The converter 46 may multiply the frequency by the required conversion factor, to produce the velocity, which is indicated by the velocity meter 48. The converter 46 is preferably adjustable or programmable so that the operator may vary the conversion factor. The frequency meter 44, the converter 46 and the velocity meter 48 may be either analog or digital devices.

The gain control 28 is preferably calibrated, to indicate the gain factor which is required to produce sustained oscillations in the closed loop 30. This gain factor is an indication of the attenuation of the acoustic or seismic energy as it is progpagated through the earth material 12 between the generator 18 and the receiver 24. Thus, the gain factor is another indication of the characteristics of the earth material 12.

The filter 32 may be employed to remove or attenuate spurious or interfering signals which are picked up by the receiver 24. The filter 32 prevents such spurious signals from intefering with the accuracy of the measurements performed by the apparatus 10. Such spurious signals may include rumbles at 60 Hz or 120 Hz, produced by electrical machinery or equipment.

When the gain of the entire closed loop system 30 exceeds unity and the proper phase relationship exists, sustained oscillations are produced in the system. Such oscillations are produced in both the electrical energy and the acoustic or seismic energy 22. The gain factor between the generator 18 and the receiver 24 is less than unity, due to the attenuation of the acoustic or seismic energy as it is progatated through the earth material 12. To achieve a system gain exceeding unity, the gain or amplification of the electrical system must be correspondingly greater than unity. The system gain is the product of the fractional gain through the earth material 12, between the generator 18 and the receiver 24, and the amplifier gain through the electrical system, comprising the variable gain control 28, the amplifier 26, the filter 32, and the driver 20.

In the operation of the apparatus 10, the amplifier gain is gradually increased by increasing the gain setting of the variable gain control 28, until the system gain is greater than one or unity, as indicated by the production of sustained oscillations in the closed loop 30. The sustained oscillations are indicated by the oscilloscope 40 and the level meter 42. The inherent noise in the closed loop provides initial signals from which the sustained oscillations are built up. The frequency of the sustained oscillations is a direct measure of the propagation velocity of the acoustic or seismic waves 22 through the earth material. The propagation velocity of the seismic or acoustic waves 22 through the earth material 12 will vary from about 300 meters per second to about 10,000 m/sec, depending upon the characteristics of the earth material. Thus, the measured velocity is an indication of such characteristics. The propagation velocity of the electrical signals through the electrical system is much greater, approaching the speed of light, which is $3 \times 10^8$ m/sec. This applies to the entire electrical system, comprising the receiver 24, the transmission line 34, the variable gain control 28, the amplifier 26, the filter 32, the transmission line 36, the driver 20, the transmission line 38 and the generator 18. Due to the high propagation velocity of the electrical signals, the propagation time of the electrical signals through the electrical system is negligible compared to the acoustic velocity.

When the gain of the closed loop system is increased sufficiently to produce sustained oscillations, the frequency of such oscillations is determined by the propagation velocity of the acoustic or seismic energy through the earth material 12 across the distance D between the generator 18 and the receiver 24. Due to this relationship, the oscillation frequency is proportional to the velocity of acoustic propagation. The measured frequency can be converted into velocity by multiplying the measured frequency by the distance D along which the acoustic waves are propagated between the generator 18 and the receiver 24.

The measurement of the acoustic or seismic propagation velocity through the earth material 12 between the two bore holes 14 and 16 provides a valuable indication as to the geological structure of the earth. Such geological information is necessary for most civil engineering applications, mineral exploration, petroleum exploration, and exploration for other energy sources, such as oil shale. Exploration for water is also aided by such geological information.

The method and apparatus of the present invention can also be used to perform non-destructive evaluation of structural materials, such as steel, aluminum, and concrete, to search for inclusions, cracks and other imperfections.

The present invention has the particular advantage of providing simpler and more accurate measurements of acoustic velocities through materials to be characterized. In accordance with the present invention, the acoustic velocity is determined by measuring the frequency or period of the sustained oscillations. Such frequency or period measurement is easier and more accurate than the traditional method of directly measuring the precise travel time of an acoustic or seismic pulse through the material to be characterized. Such direct measurement of the travel time involves measuring the time lapse between the departure of the acoustic pulse from the generator and the arrival of the acoustic pulse at the receiver. Such time lapse measurements are difficult, particularly in the presence of a high noise level. The measurement of the oscillation frequency can be accomplished very easily and accurately.

The present invention has the additional advantage that the method and apparatus of the present invention can readily be employed for continuously monitoring the acoustic or seismic propagation velocity through earth material. For such an application of the present invention, the sustained oscillations are produced on a continuous basis. The frequency of such oscillations is measured continuously, or at frequent intervals, and is recorded by a chart recorder 50 or otherwise. The recorder 50 may also record the velocity. Variations in the frequency indicate changes in the earth material. Such changes may be produced by changes in temperature, moisture or stress.

Thus, the present invention can be employed for monitoring temperature changes in the neighborhood of underground storage or disposal facilities for radioactive materials. Moreover, the present invention can be employed for monitoring temperature changes as an indication of volcanic activity. Furthermore, the present invention can be employed for monitoring stress changes which may precede earthquakes and thus may be of assistance in predicting possible earthquakes.

For continuous monitoring, the variable gain control 28 may advantageously include an automatic level control for maintaining the sustained oscillations at the desired level or amplitude.

It will be understood that the generator 18 and the receiver 24 do not have to be in bore holes, but may engage the material to be tested at surface locations or at any suitable location.

Various other modifications may be employed within the true spirit and scope of the present invention, as defined in the following claims.

I claim:

1. Apparatus for characterizing materials, said apparatus comprising an acoustic generator for converting electric energy into acoustic energy and for supplying such acoustic energy to the material to be characterized at a first location, the acoustic energy being propagated through the material, an acoustic receiver for receiving the acoustic energy from the material at a second location and for converting the received acoustic energy into electrical signals, an amplifier system connected between said receiver and said generator for amplifying the electrical signals from said receiver and supplying corresponding amplified electrical energy to said generator, said generator, said receiver and said amplifier being arranged for inclusion in forming a closed loop with the material, said amplifier system having sufficient regenerative gain to produce sustained oscillations in said closed loop which indicate the characteristics of the material through which said acoustic energy is being propagated, and indicating means for indicating the character of said oscillations as an indication of the character of said material.

2. Apparatus according to claim 1, in which said indicating means comprise frequency measuring means for measuring the frequency of said oscillations.

3. Apparatus according to claim 1, in which said indicating means comprise velocity indicating means for measuring the frequency of said oscillations and for converting the frequency into an indication of the velocity of the propagation of the acoustic energy through the material.

4. Apparatus according to claim 1, in which said indicating means include velocity indicating means for measuring the frequency of said oscillations and for converting the frequency into an indication of velocity by multiplying the frequency by the distance through the material between said transmitter and said receiver.

5. Apparatus according to claim 1, in which said amplifier system comprises a gain control for adjusting the gain of the system to produce sustained oscillations.

6. Apparatus according to claim 1, in which said amplifier system includes a calibrated gain control for adjusting the gain of the amplifier system to produce sustained oscillations while indicating the magnitude of such gain as a further indication of the character of the material.

7. Apparatus according to claim 1, in which said indicating means include frequency measuring means for indicating the frequency of said oscillations as an indication of the character of the material through which the acoustic energy is propagated, said amplifier system including a calibrated gain control for adjusting the gain of the amplifier system to produce sustained oscillations while indicating the gain as a further indication of the character of the material.

8. Apparatus according to claim 1, in which said generator comprises means for generating generally sinusoidal acoustic shear waves for propagation through the material.

9. Apparatus according to claim 1, in which said receiver comprises a geophone.

10. Apparatus according to claim 1, in which said generator comprises means for generating generally sinusoidal acoustic shear waves, said receiver comprising a geophone.

11. A method of characterizing materials, comprising the steps of supplying acoustic energy at a first location to the material to be characterized, the acoustic energy being propagated through the material, receiving the acoustic energy at a second location on the material and converting the received acoustic energy into electrical signals, amplifying the electrical signals to produce amplified electrical energy, said steps of supplying, receiving and amplifying being performed inclusively in a closed loop that also includes the material, converting the amplified electrical energy into said acoustic energy at said first location, said amplifying step being carried out with sufficient regenerative amplification to produce sustained oscillations of the electrical energy and the acoustic energy in the closed loop and indicating the frequency of said oscillations as an indication of the character of the material.

12. A method according to claim 11, in which said indicating step includes measuring the frequency of said oscillations.

13. A method according to claim 11, in which said indicating step includes measuring the frequency of said oscillations and converting the frequency into an indication of the velocity of the propagation of the acoustic energy through the material.

14. A method according to claim 11, in which said indicating step includes measuring the frequency of said oscillations and multiplying the frequency by the distance of acoustic propagation through the material to produce an indication of the velocity of acoustic propagation through the material.

15. A method according to claim 11, in which the amplifying step includes adjusting the regenerative amplification to produce sustained oscillations.

16. A method according to claim 11, in which the amplifying steps includes adjusting the gain factor of the regenerative amplification to produce sustained oscillations, and indicating the magnitude of said gain factor as a further indication of the character of the material.

17. A method according to claim 11, in which said indicating step includes measuring the frequency of said oscillations as an indication of the character of the material, said amplifying step including adjusting the gain factor of said amplification to provide sufficient regenerative amplification to produce sustained oscillations, and indicating said gain factor as a further indication of the character of the material.

18. A method according to claim 11, in which said acoustic energy is produced in the form of a generally sinusoidal acoustic shear wave for propagation through the material.

19. A method for measuring stress in the material of a volume of earth between first and second boreholes, including the steps of:

generating acoustic energy in the form of sinusoidal shear waves in the first borehole by means of a generator that converts electrical energy to acoustic energy, said acoustic energy being directed toward the second borehole;

receiving the acoustic energy in the second borehole and converting the received energy into electrical signals;

amplifying the electrical signals for transmission to the generator;

said steps of generating, receiving said amplifying being performed inclusively in a closed loop that also includes the material.
said amplification having sufficient regenerative gain to produce sustained oscillations in the closed loop which indicate the stress of the material of the volume of earth through which the acoustic energy is being transmitted,
said generating, receiving and amplifying being done in the closed loop, the inherent noise in the closed loop providing initial signals to build sustained oscillations.

* * * * *